United States Patent
Benecke et al.

[11] Patent Number: 6,063,086
[45] Date of Patent: May 16, 2000

[54] BIPOLAR ENDOSCOPIC INSTRUMENT

[75] Inventors: Rainer Benecke, Todendorf; Stefan Völzow, Hamburg, both of Germany

[73] Assignee: Olympus Winter & Ibe GmbH, Hamburg, Germany

[21] Appl. No.: 09/109,943

[22] Filed: Jul. 6, 1998

[30] Foreign Application Priority Data

Jul. 10, 1997 [DE] Germany ............................ 197 29 461

[51] Int. Cl.⁷ .................................................. A61B 18/18
[52] U.S. Cl. ................................................. 606/51; 606/48
[58] Field of Search ........................... 606/46, 45, 48–52, 606/205–208

[56] References Cited

U.S. PATENT DOCUMENTS

| | | | |
|---|---|---|---|
| 4,887,612 | 12/1989 | Esser et al. | 606/208 |
| 5,697,949 | 12/1997 | Giurtino et al. | 606/205 |
| 5,853,412 | 12/1998 | Mayenberger | 606/51 |
| 5,976,132 | 11/1999 | Morris | 606/49 |

FOREIGN PATENT DOCUMENTS

| | | |
|---|---|---|
| 43 12 284 | 11/1993 | Germany . |
| 296 04 191 | 4/1996 | Germany . |

*Primary Examiner*—Michael Peffley
*Attorney, Agent, or Firm*—Walter C. Farley

[57] ABSTRACT

A bipolar endoscopic instrument has a tubular stem fitted at its distal end with two arms pivotally supported on a shaft. The arms are pivoted by actuating an axially displaceable push/pull element mounted in the stem. The arms are connected through mutually electrically insulated leads to the terminals of a high-frequency power source, the shaft having two mutually insulated, electrically conductive segments each electrically connected to one of the electrical leads and the arm associated with this lead.

14 Claims, 3 Drawing Sheets

BIPOLAR ENDOSCOPIC INSTRUMENT

FIELD OF THE INVENTION

The invention relates to a bipolar endoscopic instrument having a tubular stem with two arms mutually pivotably supported on a shaft mounted at the distal end of said stem, the pivoting motion of the aims being caused by a push/pull element mounted in axially displaceable manner in the stem, the arms being connected by mutually insulated electric power leads to the terminals of a high-frequency voltage source.

BACKGROUND OF THE INVENTION

An example of an instruments of this type includes bipolar gripping forceps to grip and coagulate tissue. However, such instruments also may be other devices having different functions such as scissors.

In general, bipolar instruments comprise two arms pivotable about a support shaft and each is electrically conductively connected to a different terminal of a high frequency (hf) generator. The arms are made to pivot by a push/pull element displaceably mounted in the stem. The distal end of the push/pull element is connected to the arms by a suitable mechanism which converts axial displacement of the element into a pivoting motion of the arms. Said mechanism illustratively may be a knuckle joint or the like.

An instrument of this general type has been disclosed in German Gebrauchsmuster 296 04 191 which describes a coagulating gripping forceps wherein power is applied to one arm through the shank and to the other arm through the electrically conducting push/pull element. This known design is comparatively elaborate and requires careful insulation, especially in the area of the coupling between the arms and the distal end of the push/pull element also acts as an electric conductor.

SUMMARY OF THE INVENTION

An object of the present invention is to provide a bipolar endoscopic instrument wherein the power feed to the arms is significantly simplified as compared with the prior art.

This object is achieved by an instrument wherein the shaft pivotably supports the arms and at the same time also assumes an electrical conducting function for both power leads. For that purpose, the shaft comprises two mutually insulated, electrically conductive zones, each one electrically connected to one of the two arms, and each one in contact with one of the two leads leading to the hf generator, the contact in the case of rotating zones being for instance a sliding contact.

Advantageously, the shaft comprises a cylindrical insulating element made of a non-conductive material insulating from each other two electrically conductive zones formed by two conductive sleeves. Illustratively, the cylindrical insulating element may extend the full length of the shaft with the conductive sleeves slipped over its ends. It will be appreciated that the sleeves are held so as to stay out of contact with one another. For that purpose, the insulating element may be fitted for instance with a centrally peripheral projection spacing the sleeves from each other. To achieve problem-free mounting of the shaft, the projection approximately corresponds to the sleeve wall thickness so that the shaft diameter can be uniform over its full length. A metal (steel) or ceramic core may be inserted into the insulating element to impart higher mechanical strength to it.

Moreover, to increase the bending strength, one of the two electrically conductive sleeves may be fitted with a larger wall thickness. Taking into account the small shaft cross-section available, the insulating element, which in any event is made of an elastic plastic, extends over only part of the length of the shaft. Therefore, an electrically conductive sleeve having substantially a larger wall thickness can be provided in the remaining, free portion of the shaft than is possible in the next discussed design. As a result the shaft's bending strength is substantially increased over its full length.

The insulating element furthermore might be configured in such a way that one of its ends may receive one of the sleeves in a centered manner whereas a slip-on zone is formed at the opposite end of the insulating element. In such a configuration, the insulating element would align all essential shaft components with each other. As a rule, however, even this embodiment comprises a central and illustratively metallic core simultaneously enhancing strength and, regardless of insulating-body design, mutually aligning, i.e. centering the individual shaft components.

As is known to the expert, little space is available in the distal region of the instruments of this type. Consequently, the spacings between electrically conductive zones which must be insulated from each other are minute. Therefore, the insulating materials employed must be selected to offer adequate dielectric (breakdown) strength, and this selection is readily performed by the expert regarding the known spacings and operational voltages. Plastics having high bending strengths, temperature resistance and breakdown strength are preferred insulators. However, ceramics also may be used as insulators. Ceramics offer the advantage over plastic that, in the presence of saline water, the almost inevitable weak currents cannot cause carbonization at the insulation surface. On the other hand, ceramics are more susceptible to breaking.

Regardless of the insulating material used, dielectric breakdowns may arise wherever an electrical connection caused by conducting air is possible between two mutually insulated, electrically conductive zones. Especially critical in this respect are the contact areas of mutually adjoining parts in which gaps may be created following improper assembly, for instance connecting a metallic core zone with an electrically conductive sleeve. Such gaps are critical because the minute spacings between the conductive zones are inadequate to reliably preclude dielectric breakdown through conductive air. Therefore it is necessary to, for example, bond the mutually adjoining shaft components, a cement of high breakdown strength being required. Bonding during assembly is an elaborate procedure. If the assembly is to be substantially cement-free, then, according to another embodiment of the invention, further insulating components are optionally provided to lengthen the path of a current between the electrically conductive zones. Such components in turn may be again in the form of sleeves (FIG. 5).

Another way to avert any undesired currents is to coat metallic areas not used in electrical conduction with an insulating material. This is especially significant at the alms if only their parts used in actual coagulation were conductive. Thin coatings entailing no significant diameter enlargement may be used to insulate the arms and individual shaft components such as the metal core.

Using the shaft of the invention, the power can be fed in exceedingly simple ways to the arms. The power leads from the hf generator may be shifted to mutually opposite sides into the stem and may terminate with their ends in boreholes in this stem, the shaft by its ends being received in those boreholes. The ends of the power leads illustratively may be sliding contacts resting against the shaft.

This design provides in an especially simple manner two power feeds which are mutually insulated over the full length of the instrument, for the arms.

In this design, only insulation in the mechanism converting the push/pull motion into a pivoting motion need be provided. Conventional arms are fitted with levers extending from the shaft in the proximal direction into the stem where they act on a suitable mechanism. Typically, the mechanism is a knuckle joint comprising comparatively many mutually moving pairs that may easily drop off and jeopardize the patient; insulation in this design is laborious. Therefore, a further embodiment of the invention provides that a cam mechanism be used to pivot the arms. Illustratively, such a cam mechanism comprises a coupling element at the distal end of the push/pull element containing two slots (or cams) running obliquely to the stem axis. The levers of each arm have a laterally projecting stub slidingly received in one of the two slots. When the coupling element is displaced due to the actuation of the push/pull element, the stub guided in the elongated slot is deflected and pivots the arm associated to it. The cam mechanism may be varied to comprise a coupling element with laterally projecting stubs which in turn are slidingly guided in slots or elongated apertures in the arms.

When using a cam mechanism, the insulation of the metallic levers or of the arms possibly connected to them in conductive manner only requires that the coupling element have correspondingly insulated properties. In the simplest case the element as whole is of insulating material. However, the slots may be made as separate parts from other materials such as metals and be inserted into the element otherwise made of an insulator. Strength is increased in this manner.

In another advantageous embodiment of the invention, a slider running in the distal direction is fitted on the coupling element. The slider comprises an elongated slot enclosing the shaft. Upon actuation of the push/pull element, the slider reciprocates axially and thereby expels any liquid between the portions of the arms near the shaft. As a result a sharp reduction in the otherwise frequent leakage currents can be achieved.

Another embodiment concerns the aims. An especially simple design consists in making the arms and the levers being made of a metallic material, that is being electrically conductive. A safety circuit inserted into the hf generator typically used in such applications prevents current interruption and shorts in case the arms should touch each other.

As already mentioned above, preferably the arms are made conductive only in zones in mutually opposite segments. Those segments which, for instance, when closing the arms will move toward each other are opposite. Gripping forceps comprising such arms allow extremely precise coagulation or other electro-surgical work. The forceps illustratively may be manufactured by applying an insulating coating to the arms made of conductive material and then removing this coating in the areas of desired conductivity.

BRIEF DESCRIPTION OF THE DRAWINGS

The invention is described below with reference to several Figures showing different illustrative embodiments.

DESCRIPTION OF PREFERRED EMBODIMENTS

Figure 1:
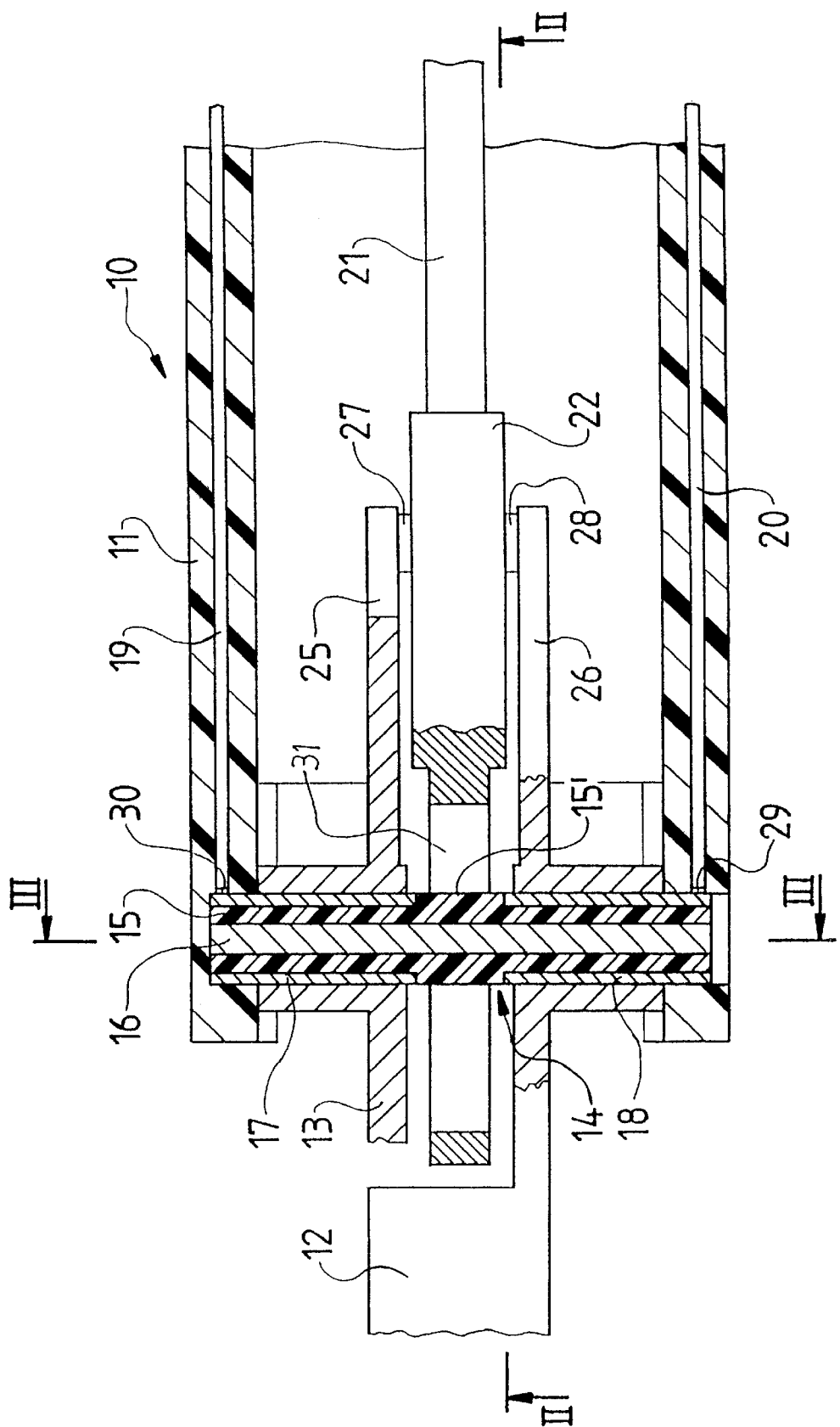
FIG. 1 is a section of the distal end of the stem in a first embodiment of the invention.
Figure 2:
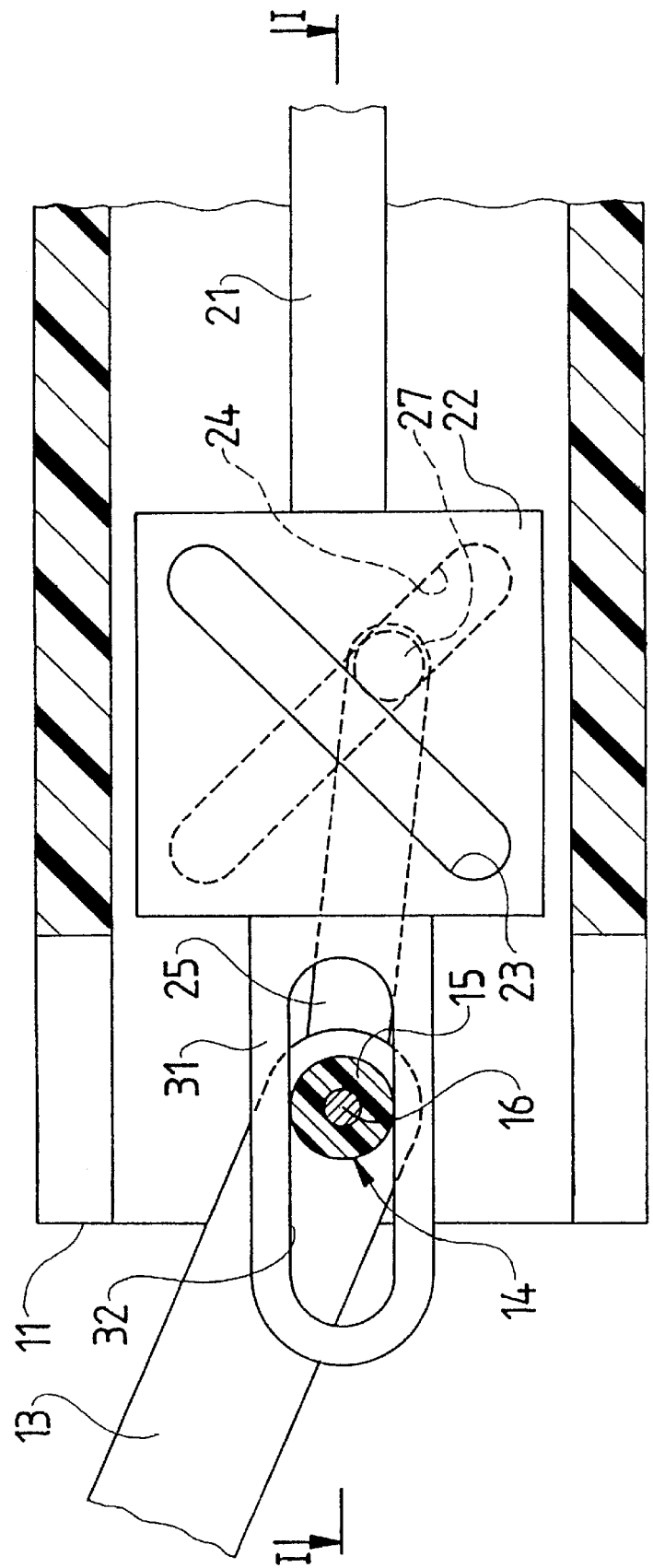
FIG. 2 is a section along line II—II of FIG. 1.

FIGS. 1 and 2 show the distal region of a bipolar endoscopic instrument 10 which in this case is a gripping forceps. Instrument 10 comprises a stem 11 made of an insulating material such as liquid crystal polymer (LCP), polyaiyletherketone (PEEK) or polyphenylen sulfone (PPSU) and which at its distal end terminates in two mutually opposite lateral forks (FIGS. 3–6).

Two mutually pivotable forceps arms 12 and 13 are mounted on instrument 10 and are held on a shaft 14. Shaft 14 has a cylindrical insulating element 15 of electrically non-conductive material into which is inserted a cylindrical core 16 of a metallic material such as steel to reinforce the insulating element. Electrically conductive sleeves 17 and 18 are mounted on insulating element 15 to ensure on one hand conductive contact with arms 12 and 13 and on the other hand contact with leads 19 and 20 ensuring connection to the terminals of an hf generator schematically shown at 34. Sleeves 17 and 18 are spaced apart from each other by a central enlargement 15' of the periphery of insulating element 15. One end of the insulating element may be sealed by a transverse wall 15" (FIG. 3) in which event central core 16 is sheathed entirely in insulation in this region. As shown, the thickness of enlargement 15' corresponds to the wall thickness of sleeves 17 and 18 and, as a result, the outer diameter of shaft 14 is essentially uniform over its full length. In this manner, shaft 14 can be inserted during assembly into stem 11 and through the boreholes of arms 12 and 13 without difficulty.

A push/pull element 21 extends inside stem 11 and is affixed at its end to a coupling element 22. Diagonal slots 23 and 24, shown in FIG. 2, are in opposite sides of coupling element 22. Stubs 27 and 28 laterally projecting from levers 25 and 26 are received in sliding relationship in slots 23 and 24. Levers 25 and 26 extend proximally from alms 12 and 13, respectively. When coupling element 22 is axially displaced by the push/pull element inside the stem 11, the stubs 27 and 28 are driven in the slots of coupling element 22 and pivot levers 25 and 26 and hence the arms 12 and 13 are made to pivot in opposite directions.

As mentioned above, the special design of the shaft allows feeding power to both arms 12 and 13 in an especially simple and mutually insulated manner. The current leads 19 and 20 can be installed in simple manner in stem 11 which, as already mentioned, comprises an electrical insulating material. It is enough to mount, for instance, sliding contacts 29 and 30 at the distal ends of power leads 19 and 20, the contacts making electrical contact with sleeves 17 and 18. Such illustrative sliding contacts are of simple design and relatively malfunction-proof. Further insulation is required merely to electrically separate the arms, i.e., their levers from each other in the region of the coupling element 22. Advantageously, the coupling element 22 need not be made of an electrically conductive material. PEEK, PPSU or again LCP may be used. Also and illustratively, stubs 27 and 28 or levers 25 and 26 need not be electrically conductive everywhere. In each case when using the shown cam drive, insulation possible with economy of parts. FIG. 1 also indicates that a slider 31 is present at the coupling element 22 and extends in the proximal direction. This slider 31 is elucidated in relation to FIG. 2.

FIG. 2 again shows push/pull element 21 allowing axial displacement of coupling element 22 inside stem 1. As mentioned above, slots 23 and 24 in coupling element 22 which slidingly receive stubs 27 and 28 of levers 25 and 26. When the coupling element is displaced, these stubs are deflected and in the process pivot arms 12 and 13 (only arm 13 being shown in FIG. 2) about shaft 14. FIG. 2 further shows that the slider 31 extends as far as a region which is proximal to the shaft 14 to make possible problem-free axial adjustment, and that it comprises an elongated slot 32 in the vicinity of, and enclosing, shaft 14. When during instrument use the slider is advanced by means of coupling element 22, it will expel any liquid accumulated between the zones of the arms close to the shaft and thereby prevents possible shorting in this zone. The slider always is made of the same electrically non-conductive material as the coupling element.

FIGS. 3–6 are sectional views from which the arms and associated parts were omitted for the sake of clarity.

Figure 3:
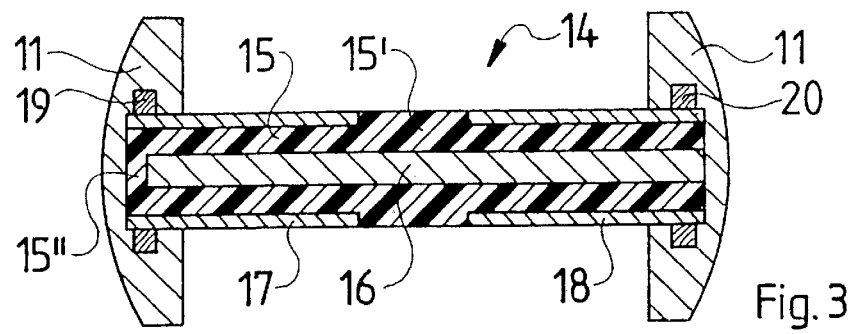
FIG. 3 is an end elevation in section in the direction of line III—III of FIG. 1, the insulating element being sealed at one of its ends contrary to the embodiment of FIG. 1.

FIG. 3, which shows the embodiment of FIG. 1 in slightly modified form, will be discussed only briefly. In this cross-section, the distal part of stem 11 forms two laterally spaced, fork-shaped zones, shaft 14 being mounted between said zones. Insulating element 15 is sealed at its end by a transverse wall 15". The entire inner surface of insulating element 15 therefore encloses in this region the mostly metallic core 16 and thereby prevents for instance dielectric breakdown between lead 19 and the metal core.

Figure 4:
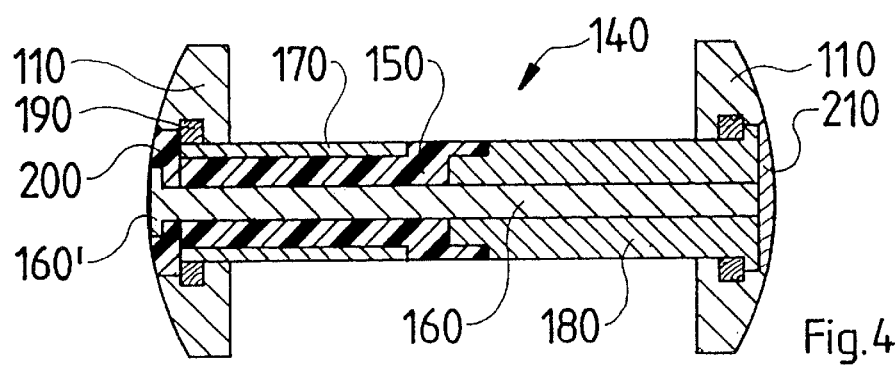
FIG. 4 is an end elevation, in section, of a second illustrative embodiment.

FIG. 4 shows a shaft 140 of a further embodiment. Shaft 140 of FIG. 4 is mounted in a stern 110 and comprises a central core 160 in the manner of the first embodiment and having a head 160'. Beginning with the head 160' the following components are slipped onto the core 160: an insulating ring 200, an insulating element 150 extending over a portion of the shaft, an electrically conductive sleeve 170 slipped on the insulating element and a further electrically conductive sleeve 180 kept from the sleeve 170 insulating element 15. The components are kept in place at one end of the core 160 by head 160' and a rotaining ring 190. The other end of the shaft is held in place by a cap 210 welded on it. The essential difference from the embodiment of FIG. 3 is that, in the embodiment of FIG. 4, insulating element 150 only extends over part of the shaft's length. Electrically conductive sleeve 180 is slipped on the core 160 at its free zone and its wall thickness is substantially larger than that of the sleeve 180 in FIG. 3. Because such electrically conductive sleeves always will be metallic or the like, shaft 140 of the embodiment of FIG. 4 has clearly increased bending strength. Otherwise the principle of the shaft design is the same as that of FIG. 3.

Figure 5:
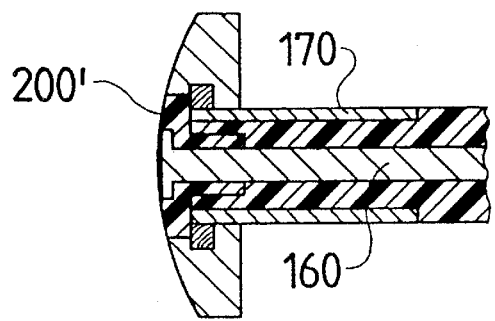
FIG. 5 is an end elevation, in section, of a third illustrative embodiment.

A problem however arises as already mentioned above, for instance, due to the boundary zone between the insulating ring 200 and the insulating element 150. Unless there be adequate bonding, a gap may from which is filled with air as the conductive medium. As regards conventional shaft dimensions, the spacings between electrically conductive sleeve 170 and metal core 160 are insufficient to preclude dielectric breakdown at all possible operational voltages. Therefore, assembly requires that the boundary surfaces be carefully cemented. Alternatively, as shown in FIG. 5, a special insulating ring 200' may be provided to extend the path which must be followed by current to arc between the sleeve 170 and the core 160. In the latter embodiment, cementing no longer is mandatory and assembly is made easier.

Figure 6:
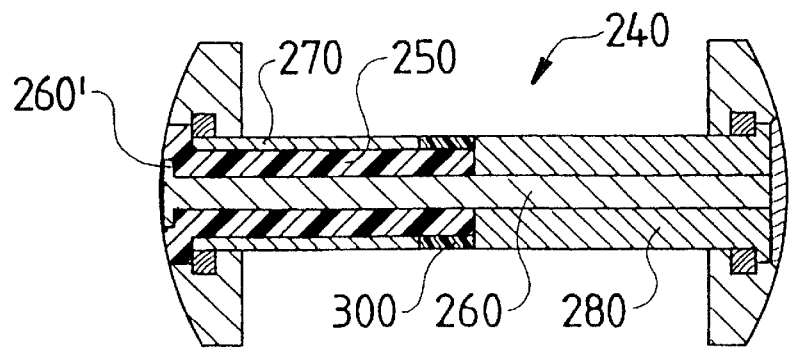
FIG. 6 is an end elevation, in section, similar to the embodiment of FIG. 5 in a slightly modified form.

Lastly, FIG. 6 shows another embodiment of a shaft 240 of the invention. Basically the shaft 240 may be designed as that shown in FIG. 4. Again a core 260 with head 260' is provided. However, contrary to the design of FIG. 4, the separate insulating ring and insulating element are absent. Instead, both components are consolidated into one insulating element 250 whereby any gap between the sleeve 270 and the core becomes so long (as in the embodiment of FIG. 5) that dielectric breakdown no longer need be expected. In this design however assembly requires an additional insulating ring 300 in the center zone to prevent dielectric breakdown between electrically conductive sleeves 270 and 280. Otherwise the embodiment of FIG. 6 is the same configuration as in FIG. 5.

What is claimed is:

1. A bipolar endoscopic instrument comprising
   a tubular stem (11) having a proximal end and a distal end;
   a shaft (14) supported at a distal end of said stem, said shaft (14) having two mutually insulated electrically conductive zones (17, 18);
   two arms pivotably supported on said shaft;
   means for causing pivoting motion of said arms, said means including a push/pull element axially displaceable in said stem and coupled to said arms to cause said arms to pivot in opposite directions; and
   electrical power leads each having one end connected to an output terminal of a high-frequency voltage source and the other ends connected respectively to said electrically conductive zones of said shaft and through said zones to said arms.

2. An instrument according to claim 1 wherein said electrically conductive zones of said shaft comprise two electrically conductive sleeves (17, 18, 170, 180, 270, 280), and a cylindrical insulating element (15, 150, 250) insulating said conductive sleeves from each other.

3. An instrument according to claim 2 wherein said insulating element (150, 250) extends over part of the length of the shaft (140, 240).

4. An instrument according to claim 2 wherein, in an assembled state of said shaft (14, 140), said insulating element (15, 150) mutually aligns said electrically conductive sleeves (17, 18, 170, 180).

5. An instrument according to claim 4 and further including cylindrical bodies (200, 200') forming insulating rings for said shaft.

6. An instrument according to claim 1 wherein said shaft comprises an insulating sleeve (15, 150) and a metal core (16) within said insulating sleeve.

7. An instrument according to claim 6 wherein said electrical power leads extend through an interior volume of said stem.

8. An instrument according to claim 1 wherein said means for causing pivoting motion includes a cam drive for coupling said push/pull element to said arms.

9. An instrument according to claim 8 wherein said cam drive comprises a coupling element at a distal end of said push/pull element, said coupling element having first and second slots extending obliquely relative to a central axis of said stem, and first and second levers having stubs engaging and guided by said slots, said levers being connected to and driving said arms.

10. An instrument according to claim 1 and including an insulating layer covering electrically conductive surfaces in a distal end zone of said instrument and having no electrical function.

11. An instrument according to claim 1, wherein said arms comprise electrically conductive areas in defined, mutually opposed segments.

12. An instrument according to claim 1 wherein said means for causing pivoting motion includes a cam drive for coupling said push/pull element to said arms, said cam drive comprises a coupling element at a distal end of said push/pull element and wherein said coupling element (22) comprises an electrically non-conductive material.

13. An instrument in claim 12 wherein said coupling element comprises slots mutually configurable in an insulated manner and consist of or ceramics.

14. An instrument according to claim 11 comprising a slider (31) extending distally from said coupling element (22) to the distal side of said shaft (14).

* * * * *